United States Patent [19]

Yamagami et al.

[11] 4,372,846
[45] Feb. 8, 1983

[54] BLOOD PURIFICATION SYSTEM

[75] Inventors: Seiji Yamagami, Sakai; Hirohiko Nonaka, Oimachi; Tuneyoshi Shimonaru, Suita; Koichi Takashima, Kakogawa; Yasuhiko Kato, Oimachi, all of Japan

[73] Assignee: Daicel Chemical Industries Ltd., Osaka, Japan

[21] Appl. No.: 244,319

[22] Filed: Mar. 16, 1981

[30] Foreign Application Priority Data

Mar. 22, 1980 [JP] Japan ................................. 55/36751

[51] Int. Cl.³ .............................................. B01D 31/00
[52] U.S. Cl. ........................................ 210/86; 210/87; 210/433.2
[58] Field of Search .................... 210/433.2, 321.3, 85, 210/86, 87, 96.2, 90

[56] References Cited

U.S. PATENT DOCUMENTS 3,946,731  3/1976  Lichtenstein .......................... 210/90

FOREIGN PATENT DOCUMENTS 2629717  5/1978  Fed. Rep. of Germany ... 210/321.3
54-154196  2/1979  Japan ................................. 210/500.2

Primary Examiner—Frank A. Spear, Jr.
Attorney, Agent, or Firm—Hubbell, Cohen, Stiefel & Gross

[57] ABSTRACT

The invention relates to a blood purification system especially useful as an artificial kidney system. When the blood of the patient is purified by a filter, the volume of filtrate from the filter is measured accurately and the volume of a substitution fluid supplied to the patient is measured accurately. The blood is purified while the two volumes are being maintained in balance accurately.

8 Claims, 7 Drawing Figures (II)

BLOOD PURIFICATION SYSTEM

BACKGROUND OF THE INVENTION

1. Field of the Invention

The present invention relates to a blood purification system, and more particularly to a system in which blood is purified with a filter and which is effectively usable as an artificial kidney system.

2. Description of the Prior Art

Blood purification systems for hemofiltration are used typically as artificial kidney systems. Generally when artificial kidney systems are used for therapy, the filter discharges a filtrate (hereinafter referred to as "total filtrate") which is discarded. The portion of the total filtrate corresponding to the body weight loss can be discarded merely as the "removal filtrate", but when the excess of the filtrate other than the removal filtrate is discarded, the purified blood must be given a substitution fluid in an amount equal to the amount of the excess to maintain the water balance of the patient.

It is known that most optimally the living body should be given the replenishment continuously at the same rate as the discharge of the excess filtrate. To meet these requirements, therefore, it is critical for the artificial kidney system to measure the amounts of the total filtrate, removal filtrate, excess filtrate and substitution fluid.

To supply the substitution fluid continuously in balance with the excess filtrate, systems have been proposed which include those of the volume control type as disclosed typically in Published Unexamined Japanese Patent Application No. 154196/1979 and those of the weight control type a typical example of which is disclosed in U.S. Pat. No. 4,204,957. The former disclosed system is an improvement over the prior art in which the desired amounts were measured only under the control of the speed of rotation of a metering pump and comprises an electromagnetic flow meter for affording measurements with improved accuracy. However, since the system still employs a metering pump for measuring the amount of the removal ultrafiltrate as in the prior art, the system has the serious drawback that the overall accuracy of the system as an artificial kidney system is dependent on the precision of the metering pump and therefore is not higher than is achieved by other conventional systems. The latter system is of the weight measuring type which involves the necessity of storing the whole amount of the ultrafiltrate and using two balances. Accordingly the system has the drawbacks of being large-sized in its entirety, requiring a large space for installation, including a complex measuring mechanism which must be set in place with care (e.g. to assure the horizontal position of the mechanism) and having greatly reduced portability.

The present invention aims to overcome the foregoing drawbacks and provides an artificial kidney system which can accurately measure the amounts of filtrates and substitution fluid, is compact, inexpensive and convenient from the viewpoint of sanitation.

SUMMARY OF THE INVENTION

This invention provides a system which is especially suited for use as an artificial kidney system and by which blood can be filtered in balance with the supply of a substitution fluid with high accuracy for the purification of the blood.

The system of this invention comprises filter means for purifying blood; filtrate metering means including a small container, and an upper liquid level sensor and a lower liquid level sensor opposed to the side wall of the container, the container having an inlet channel connected to a filtrate outlet of the filter means and an outlet channel with a valve; blood flow adjusting means provided in an arterial channel for the filter means; a mixer provided in a venous channel of the filter means; a supply source for feeding a substitution fluid to purified blood; substitution fluid metering means including a small container, and an upper liquid level sensor and a lower liquid level sensor opposed to the side wall of the container, the container having an inlet channel connected to the supply source and equipped with a valve and an outlet channel connected to the mixer; replenishment flow adjusting means provided in the outlet channel of the substitution fluid metering means; and control means electrically connected to the filtrate metering means, the substitution fluid metering means, the blood flow adjusting means and/or the replenishment flow adjusting means.

The system according to this invention may be operated in the following way.

When the blood is purified by the filter, the filtrate discharged from the filter is led into the filtrate metering means with its valve closed until the filtrate fills its container to a level above the position where the upper liquid level sensor detects the liquid level, whereupon the valve is opened to discharge the filtrate from the container until the liquid level lowers to a level below the position where the lower liquid level sensor detects the liquid level. The valve is then closed again to fill the container. The total filtrate is run off by repeating the cycle of operation described above. During the operation, the rate of discharge of the filtrate from the filter is calculated based on the known volume of the container and the time taken for the liquid level within the container to rise from the lower liquid level detecting position to the upper liquid level detecting position. The volume of the filtrate discharged is calculated from the filtration rate and the time required for the cycle of operation.

On the other hand, the substitution fluid to be added to the purified blood is introduced into the substitution fluid metering means with its valve opened until the fluid fills its container to a level above the upper liquid level detecting position. Subsequently while interrupting the introduction of the substitution fluid by closing the valve, the substitution fluid in the container is supplied through the outlet channel to the purified blood until the liquid level lowers to a level below the lower liquid level detecting position, whereupon the valve is opened to fill the container to above the upper liquid level detecting position while maintaining the supply of the substitution fluid from the container. The valve is then closed again to lower the liquid level. Thus the purified blood is given the substitution fluid by repeating the cycle of operation described. During the operation, the rate of supply of the substitution fluid is calculated based on the known volume of the container and the time taken for the liquid level within the container to lower from the upper liquid level detecting position to the lower liquid level detecting position. The volume of the substitution fluid supplied is calculated from the replenishment rate and the time required for the cycle of operation.

The discharge volume and the supply volume are compared at a predetermined time interval to control one of these volumes based on the other so that the ratio therebetween will be in agreement with the value specified for the patient.

In this way, the blood is purified while adjusting the balance between the amount of blood filtration and amount of replenishment at a short time interval.

Also, for the control of the volume of discharge of the filtrate based on the volume of supply of the substitution fluid, it is preferable to use a filtrate flow adjusting means provided in the inlet channel of the filtrate metering means. Alternatively, for controlling the volume of supply of the substitution fluid based on the filtrate discharge, the replenishment flow adjusting means is used.

In the above explanation, the flow adjusting means is preferred to be a metering pump, such as a roller pump.

The liquid level sensor is preferred to be a photoelectric sensor comprising a light source, such as a light-emitting diode, and a photo sensor, such as a phototransistor. Such sensors are mounted usually on a holder as opposed to the side wall of the container. The sensor should not be disposed very close to the upper or lower end of the container but care should be taken to position the sensor a small distance away from the end so that the liquid level can be positioned above the upper liquid level detecting position or below the lower liquid level detecting position. More preferably a third liquid level sensor is disposed between the upper and lower liquid level sensors. To enable the sensor to detect the liquid level accurately by virtue of the refractive properties of the liquid in the container, the container is in the form of a vertical cylinder and preferably the optical axis through the light source and the photo sensor is at a distance from the center of the cylindrical container.

The control means is preferably a microcomputer system which delivers control signals to the flow adjusting means so that the ratio between the volume of discharge of the filtrate and the volume of supply of the substitution fluid will be equal to the ratio between the intended volume of total filtrate and the intended overall volume of substitution fluid (i.e. the intended volume of total filtrate minus the intended overall volume of removal filtrate). Preferably the control means controls the metering means and performs the calculations.

With the system of this invention, the upper dead point where the ascent of the liquid level changes to descent or the lower dead point where the descent of the level changes to ascent is intentionally located away from the upper or lower liquid level detecting position, so that a mechanical delay of the system, such as a delay in the operation of the valve for the metering means, can be absorbed, while the inner wall of the container is less prone to soiling at the detecting position, thus permitting the sensor to detect the liquid level with improved accuracy. Additionally the overall system is compact, inexpensive and sanitary.

Further with the third liquid level sensor provided, the metering means can be checked for malfunctions, while when either one of the upper and lower sensors fails, the normal sensor and the third sensor will operate to continuously meter the liquid, thus preventing an interruption of the operation of the system even in the event of a failure, hence advantageous.

DESCRIPTION OF THE PREFERRED EMBODIMENTS

Figure 1:
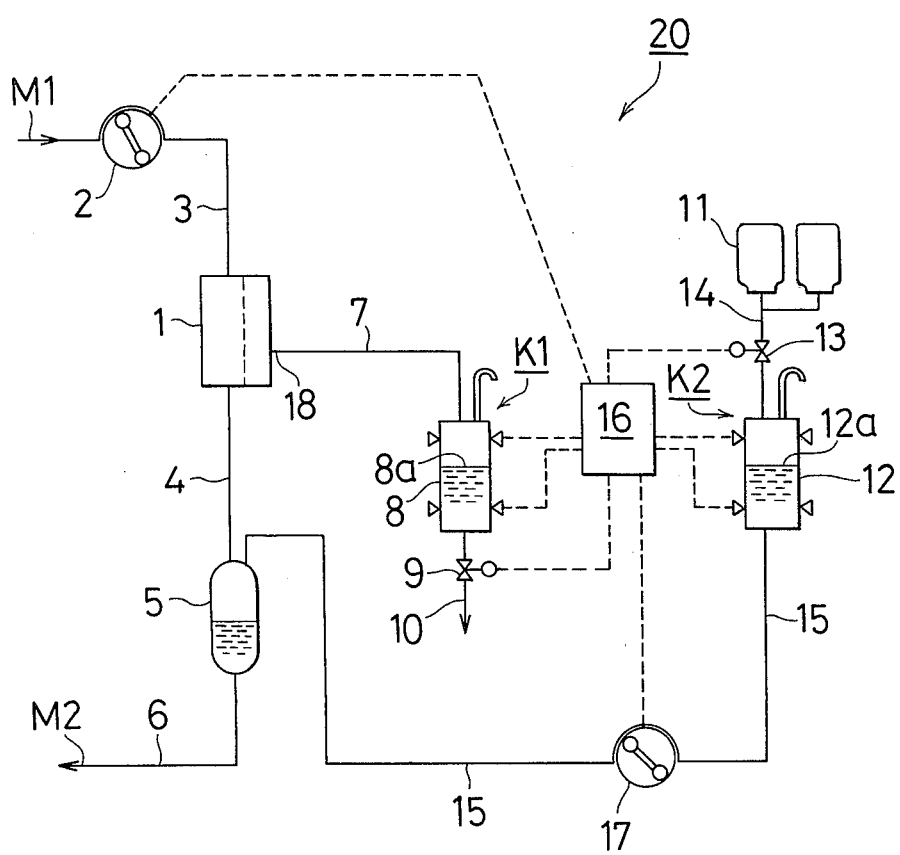
FIG. 1 is a diagram showing the construction of a blood purification system embodying the present invention.

The present invention will be described below with reference to the embodiments shown in the drawings.

FIG. 1 show an embodiment 1 of this invention for purifying blood. The blood from a connection M1 to an artery is led through an arterial channel 3 into a filter 1 by a pump 2. The blood purified by the filter 1 is passed through a venous channel 4 into a mixer 5, from which the blood is sent to a connection M2 to a vein via a venous channel 6. The filtrate is sent out from a filtrate outlet 18 of the filter 1 and passed through an inlet channel 7 into a small container 8 of a filtrate metering unit K1, from which it is run off through an outlet channel 18 with a valve 9 and wholly discarded. A tank 11 contains a susbstitution fluid, which is led through an inlet channel 14 with a valve 13 into a small container 12 of a substitution fluid metering unit K2, from which the substitution fluid is led through an outlet channel 15 into a metering pump 17 which is driven by a pulse motor. The substitution fluid is then sent to the mixer 5, in which it is added to the purified blood. Indicated at 16 is a control unit which is electrically connected to the filtrate metering unit K1, pump 2, substitution fluid metering unit K2 and metering pump 17 as indicated in broken lines.

Figure 2:
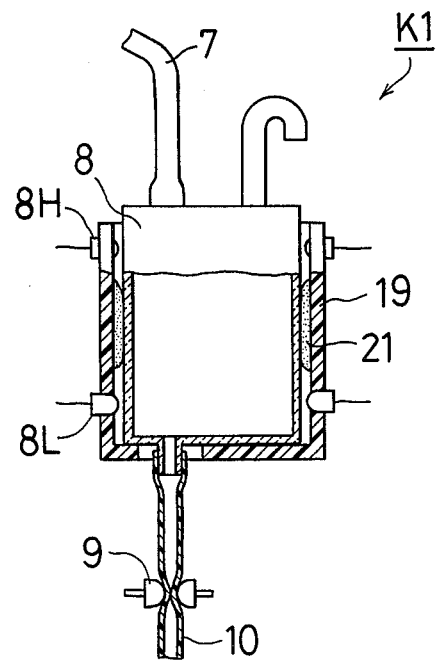
FIGS. 2 (I) and (II) show a filtrate metering unit included in the system of FIG. 1, FIG. 2 (I) being a side elevation partly broken away, and FIG. 2 (II) being a cross sectional view.
Figure 2:
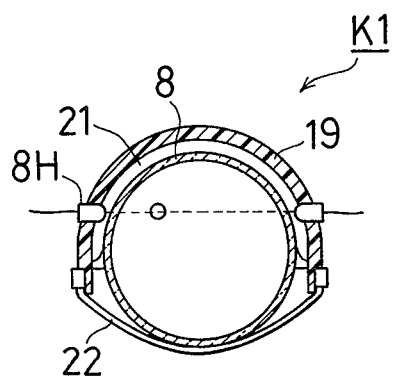

FIGS. 2 (I) and (II) show the filtrate metering unit K1 in greater detail. The container 8, the interior volume of which is known, is in the form of a cylindrical container made of transparent rigid plastics and is provided with flexible plastics tubes serving as the inlet channel 7 and the outlet channel 10. The valve 9 on the outlet channel 10 is a pinch valve. A holder 19 tightly but detachably holds the container 8 with a cushioning member 21 and a belt 22. An upper liquid level sensor 8H and a lower liquid level sensor 8L, each comprising a light-emitting diode and a phototransistor, are attached to the holder 19. The optical axis through the diode and the phototransistor is at a small distance away from the center of the container 8, by which a critical detection of the liquid level in the container can be achieved. The interior volume V1 of the container 8 between the upper and lower liquid level detecting positions is accurately measured and is therefore known.

Figure 3:
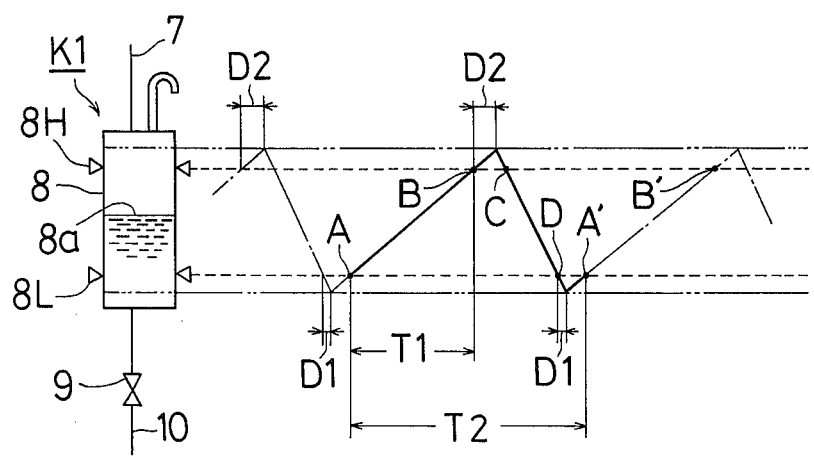
FIG. 3 is a diagram illustrating the movement of liquid level within the filtrate metering unit.

FIG. 3 is a diagram illustrating the movement of the level of the filtrate in the filtrate metering unit K1.

First, when the filtrate starts to flow into the container 8 with the valve 9 closed, the liquid surface 8a gradually rises and is detected by the lower sensor 8L at point A, where one cycle begins. The surface 8a further rises and is detected by the upper sensor 8H at point B. Upon the lapse of time D2 after the detection of the liquid surface 8a at point B, the valve 9 is opened, permitting the surface 8a to start descending. The liquid surface 8a moves past point C, i.e. the position of the upper sensor 8H, and reaches point D where the lower sensor 8L is positioned. Upon the lapse of time D1 after the detection of the surface 8a at point D, the valve 9 is closed. The filtrate now starts filling the container again, and the ascending liquid surface 8a is detected by the lower sensor 8L at the second point A', whereupon one cycle is completed which takes a period of time T2. The volume of filtrate, R1, discharged from the filter 1 per unit time (namely, substantially, the filtration rate) can be calculated based on the known volume V1 and the time T1 taken for the liquid level to rise from point A to point B. The volume of filtrate Vs discharged during the period T2 is given by the filtration rate R1 multiplied by the period T2.

In connection with the operation of the filtrate metering unit K1, the control unit 16 chiefly performs the following calculations and control function.

(1) Calculation of the rate of discharge of the filtrate, R1n, per unit time for every batch metered.

$$R1n = V1/T1n$$

(2) Calculation of the time required for each cycle, namely period T2n, and the volume of filtrate, Vsn, discharged during the cycle.

$$Vsn = R1n \times T2n$$

(3) Calculation of the time T elapsed after the start of filtration, and the volume of filtrate, V, discharged during the time T.

$$T = \sum_n T2n, \text{ and } V = \sum_n Vsn$$

(4) Opening and closing of the valve 9 in response to the signals from the liquid level sensors 8H and 8L.

If desired, a correction is made for the volume of filtrate discharged after the start of filtration until the liquid level moves past the lower sensor 8L, based on the discharge rate R1₁ obtained from the first cycle.

Figure 4:
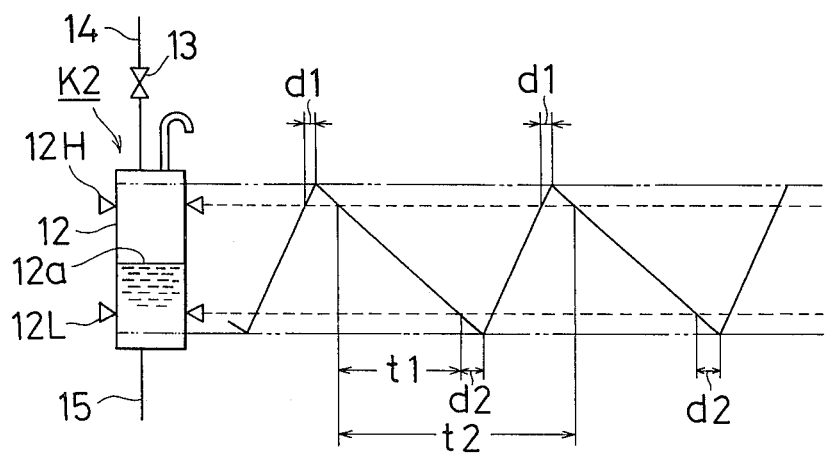
FIG. 4 is a diagram illustrating the movement of liquid level within a substitution fluid metering unit included in the system of FIG. 1.

The substitution fluid metering unit K2 to be described below has substantially the same construction as the filtrate metering until K1 shown in FIG. 2, except that the pinch valve 13 is mounted on the inlet channel 14. FIG. 4 shows the movement of the liquid level in the substitution fluid metering unit K2.

The valve 13 is opened to fill the container 12 with the substitution fluid, before the start of filtration. Then, the filtration is started and simultaneously the metering pump 17 may be initiated into rotation at a predetermined speed to start the replenishment. Preferably the pump 17 is rotated at the speed in accordance with the volume of discharged filtrate which is obtained by one cycle of filtrate metering operation. The substitution fluid is metered upon a descending time which is in reverse manner as the metering of the filtrate upon its asending time. The volume of substitution fluid supplied per unit time (namely, substantially, the replenishment rate), R2, is calculated from the known volume V2 and the time t1 required for the liquid surface 12a to descend from the position of the upper sensor 12H to the lower sensor 12L.

In connection with the substitution fluid metering operation, the control unit 16 chiefly performs the following calculations and control function.

(1) Calculation of the rate of supply of the substitution fluid, R2n, per unit time for every batch metered.

$$R2n = V2/t1n$$

(2) Calculation of the time required for each cycle, namely period t2n, and the volume of substitution fluid, V'sn, supplied during the cycle.

$$V'sn = R2n \times t2n$$

(3) Calculation of the volume of substitution fluid, V', supplied after the start of filtration.

$$V' = \Sigma V'sn$$

(4) Opening and closing of the valve 13 in response to the signals from the liquid level sensors 12H and 12L.

In this way, the filtrate or substitution fluid is metered by the system of this invention.

The control unit 16 comprises a microcomputer system which preferably has an input terminal unit, such as a digital switch, which is used for entering the intended volume of total filtrate, the intended overall volume of removal filtrate, and the time interval at which the metering pump 17 is adjusted for holding the filtrate discharge and substitution fluid supply in balance.

At the time interval (for example, every two metering batches) during filtration, the difference $V - V'$ is determined and is compared with the volume of filtrate to be removed during the lapse of time concerned based on the intended overall volume of removal filtrate. If there is any difference therebetween, the speed of the metering pump 17 is controlled for correction. The therapy is completed usually when the difference $V - V'$ becomes equal to the overall volume of removal filtrate. Preferably the volume of filtrate to be removed is the value obtained by dividing the volume V of filtrate discharged during the lapse of time concerned by the intended volume of total filtrate and multiplying the quotient by the intended overall volume of removal filtrate. Consequently it can be said that the control unit 16 operates to keep the ratio of the substitution fluid supply volume V' to the filtrate discharge volume V constant. The output of the metering pump 17 and the speed of rotation of the pump are in a predetermined relationship.

It will be understood that the intended volume of total filtrate, the intended overall volume of removal filtrate, etc. are changeable during the therapy, if desired.

The containers 8 and 12, which are variable in size as desired, may preferably have the same interior volume, for example, of 40 cc to 150 cc, preferably about 80 cc. Preferably the volume thereof between the upper and lower liquid level detecting positions is about 50 cc. Further preferably, the containers 8 and 12 may be so sized that the ratio T1/T2 or t1/t2 will be at least 5/6.

The blood purification system 20 described above is compact, sanitary and inexpensive. Since the metering units are so arranged as to preclude their malfunctions and to absorb the time delay to be involved in the operation of the valves in response to the signals from the sensors, the liquids can be metered with high accuracy.

Figure 5:
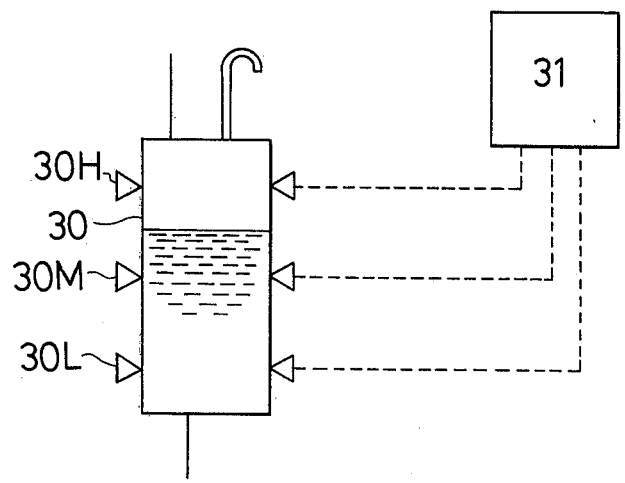
FIG. 5 is diagram illustrating a modification of the metering unit.

FIG. 5 shows another preferred embodiment of the metering means. A container 30 has a photoelectric liquid level sensor 30H at an upper portion thereof, a photoelectric level sensor 30L at a lower portion, and a third photoelectric liquid level sensor 30M at the midportion. The third sensor 30M serves to check the metering means for proper operation. Preferably a control unit 31 is adapted to estimate the time to be required for the liquid surface to reach the upper sensor 30H, based on the speed of rise of the liquid surface from the lower sensor 30L to the middle sensor 30M. If the actual time taken differs greatly from the estimation, an alarm goes off to indicate that some trouble has developed. Alternatively the control unit 31 estimates the time to be required for the liquid surface to reach the lower sensor 30L, based on the speed of descent of the liquid surface from the upper sensor 30H to the middle sensor 30M, so that if the actual time taken differs greatly from the estimation, an alarm goes off similarly. Further preferably, the control unit 31, in the event of a trouble occurring and when detecting the malfunction of one of the sensors based on the data stored therein, continues the metering operation with use of the remaining two sensors. This prevents an interruption of the operation of the blood purification system even if one of the upper and lower sensors malfunctions.

Figure 6:
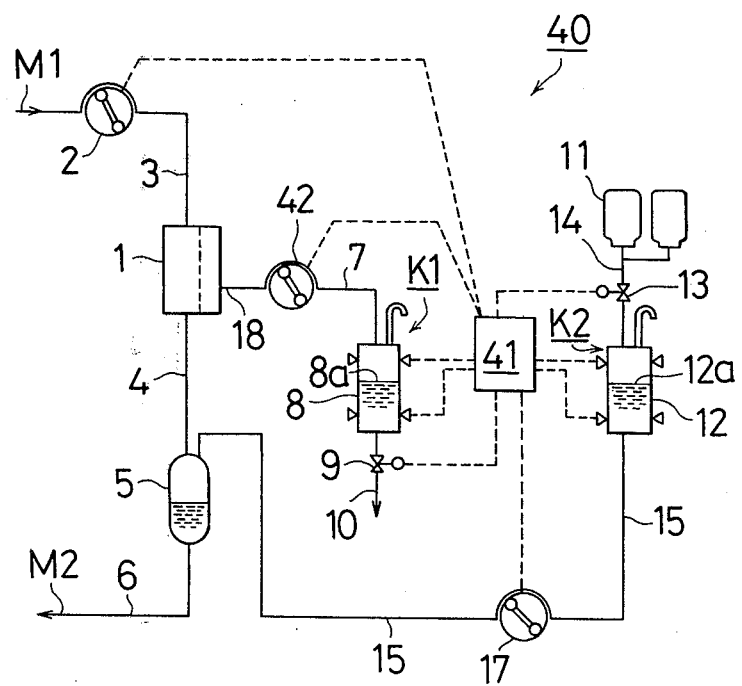
FIG. 6 is a diagram showing the construction of another blood purification system embodying the invention.

FIG. 6 shows another embodiment 40 in which a metering pump 42 is provided in the inlet channel 7 of the filtrate metering unit K1. Under a predetermined program, a control unit 41 controls the metering pump 17 to supply the substitution fluid, and based on the volume of the supply, the unit controls the metering pump 42 to control the volume of filtrate to be discharged.

To sum up, the present invention described above has the following features and advantages.

(1) Instead of directly measuring the volume of liquid in the metering container between two specified points, the system of the invention is adapted to measure only the time required for the ascent or descent of the liquid surface between the two points.

(2) The liquid surface need not be stopped at the two specified points but is allowed to overrun these points. This eliminates the malfunction of the sensors that would result from the staining of the container and absorbs delays in physical operation, permitting the metering container to operate continuously with improved accuracy.

(3) The filtrate and the substitution fluid are metered independently of each other and are related with each other only by means of the control unit.

(4) The liquid can be metered regardless, for example, of variations in the concentration of the liquid.

(5) The metering container, which is small-sized, is disposable and sanitary.

(6) The system is compact or small-sized in its entirety.

Because of these features and advantages, the present invention is very useful.

Since the above as well as other modifications and changes are intended to be within the scope of the present invention, the foregoing description should be construed as illustrative and not in the limiting sense, the scope of the invention being defined by the appended claims.

What is claimed is:

1. A system for purifying blood comprising filter means for purifying blood; filtrate metering means including a first small container, said first small container having an upper liquid level sensor and a lower liquid level sensor opposed to the side wall of the first small container, the first small container having an inlet channel connected to a filtrate outlet of the filter means and an outlet channel with a valve; blood flow adjusting means provided in an arterial channel for the filter means; a mixer provided in a venous channel of the filter means; a supply source for feeding a substitution fluid to purified blood; substitution fluid metering means including a second small container, said second small container having an upper liquid level sensor and a lower liquid level sensor opposed to the side wall of the second small container, the second small container having an inlet channel connected to the supply source and equipped with a valve and an outlet channel connected to the mixer; replenishment flow adjusting means provided in the outlet channel of the substitution fluid metering means; and control means electrically connected to the filtrate metering means, the substitution fluid metering means, the blood flow adjusting means and/or the replenishment flow adjusting means; the filtrate metering means being controllable to repeat the steps of filling the filtrate from the filter means into its container to a level above the position where the upper liquid level sensor detects the liquid level and thereafter discharging the filtrate from the container until the liquid level lowers to a level below the position where the lower liquid level sensor detects the liquid level, for the control means to calculate the volume of the filtrate discharged from the filter means based on the speed of rise of the liquid level between the upper and lower liquid level detecting positions, the substitution fluid metering means being controllable to repeat the steps of filling the substitution fluid into the second small container to a level above the position where the upper liquid level sensor detects the liquid level and thereafter running off the substitution fluid from the container until the liquid level descends to a level below the position where the lower liquid level sensor detects the liquid level, for the control means to calculate the volume of the substitution fluid supplied to the purified blood based on the speed of descent of the substitution blood level, so that the blood is purified while one of the filtrate discharge volume and the substitution fluid supply volume is being controlled based on the other volume to maintain the two volumes in a ratio specified for the patient.

2. A system as defined in claim 1 further comprising filtrate flow adjusting means provided in the inlet channel of the filtrate metering means and electrically connected to the control means.

3. A system as defined in claim 1 or 2 wherein the flow adjusting means is a metering pump.

4. A system as defined in claim 1 wherein each of the filtrate metering means and the substitution fluid metering means is provided with a further liquid level sensor between the upper liquid level sensor and the lower liquid level sensor.

5. A system as defined in claim 1 or 4 wherein each of the liquid level sensors comprises a pair of light source and photo sensor.

6. A system as defined in claim 1 or 4 wherein each of the small containers is in the form of a vertical cylindrical container.

7. A system as defined in claim 1 or 4 wherein each of the liquid level sensors comprises a pair of light source and photo sensor, each of the small containers is in the form of a vertical cylindrical container, and the optical axis through the light source and the photo sensor is at a small distance from the center of the cylindrical container.

8. A system as defined in claim 1 wherein the control means comprises a microcomputer system.

* * * * *